United States Patent [19]

Edwards

[11] 3,961,622

[45] June 8, 1976

[54] ASPIRATOR METHOD

[76] Inventor: Donald W. Edwards, 821 Peoria Ave., Dixon, Ill. 61021

[22] Filed: Sept. 9, 1975

[21] Appl. No.: 611,613

Related U.S. Application Data

[60] Division of Ser. No. 477,847, June 10, 1974, Pat. No. 3,920,001, which is a continuation-in-part of Ser. No. 58,049, July 24, 1970, abandoned.

[52] U.S. Cl. ............................ 128/2 F; 128/DIG. 5; 128/276
[51] Int. Cl.² ........................................... A61B 5/14
[58] Field of Search ............... 128/2 F, DIG. 5, 221, 128/214 R, 276, 218 N, DIG. 26

[56] References Cited
UNITED STATES PATENTS

| | | | |
|---|---|---|---|
| 2,402,306 | 6/1946 | Turkel | 128/214 R |
| 2,512,568 | 6/1950 | Saffir | 128/215 |
| 2,590,895 | 4/1952 | Scappellino | 128/221 |
| 2,952,256 | 9/1960 | Meader et al. | 128/221 |
| 3,064,648 | 11/1962 | Bujan | 128/214 R |
| 3,076,457 | 2/1963 | Copen | 128/221 |
| 3,277,893 | 10/1966 | Clark | 128/221 |
| 3,487,837 | 1/1970 | Petersen | 128/DIG. 26 |
| 3,509,880 | 5/1970 | Guttman | 128/221 |
| 3,662,754 | 5/1972 | Halloran | 128/221 |

*Primary Examiner*—Kyle L. Howell

[57] ABSTRACT

The method of taking a blood sample utilizes a cannula having a penetrating point at its distal end and an elongate lateral opening through the cannula wall on the side opposite the point. The steps of the method include sealing the lateral opening with a slidable sleeve which has an outwardly-extending base, sealing the base against the patient's skin, aligning the cannula with a blood vessel and inserting the cannula to a depth sufficient to pierce the blood vessel, and applying a slight vacuum on the cannula to withdraw blood therethrough.

2 Claims, 8 Drawing Figures

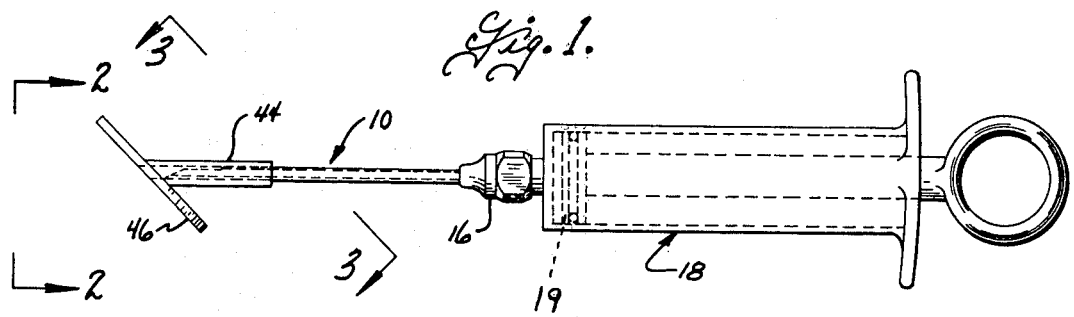
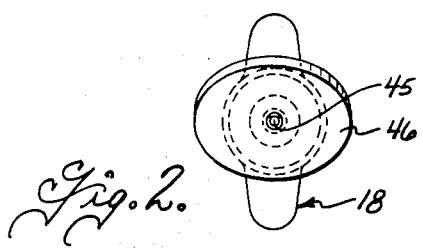
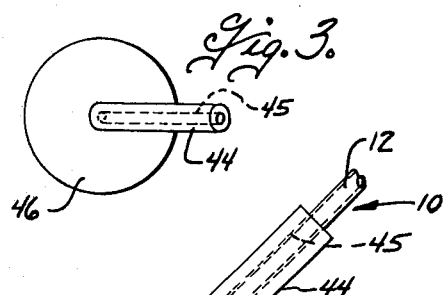
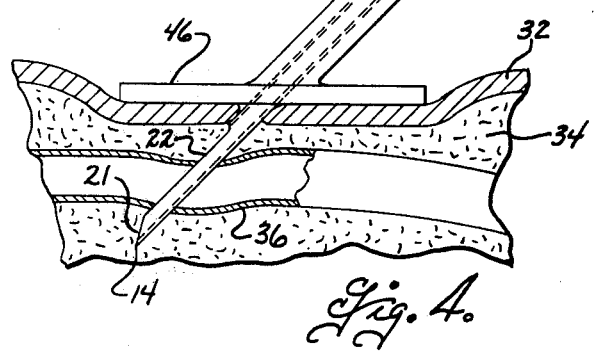
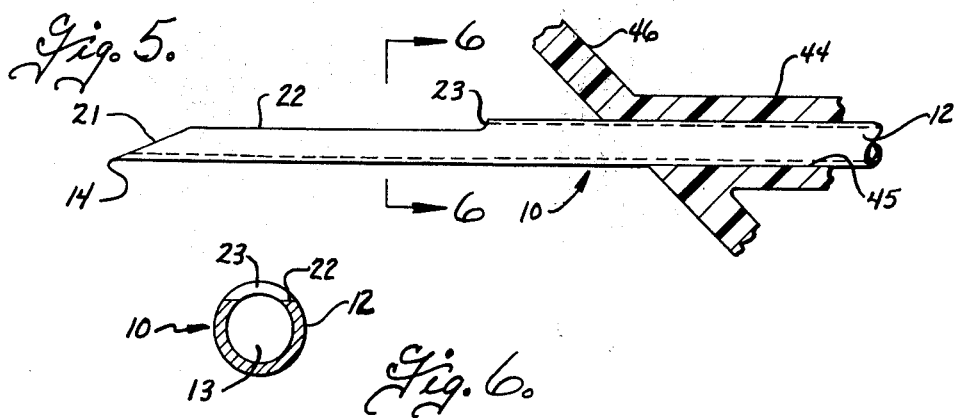

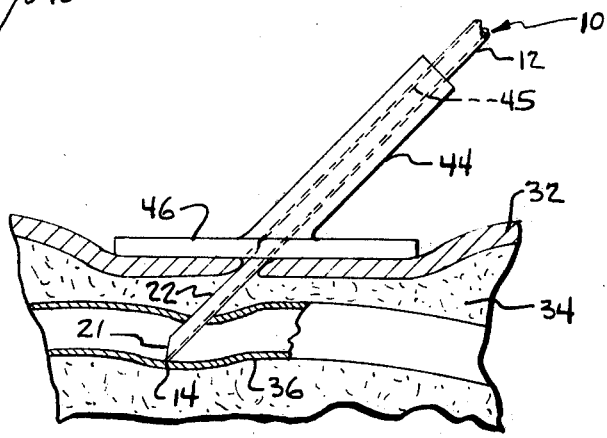
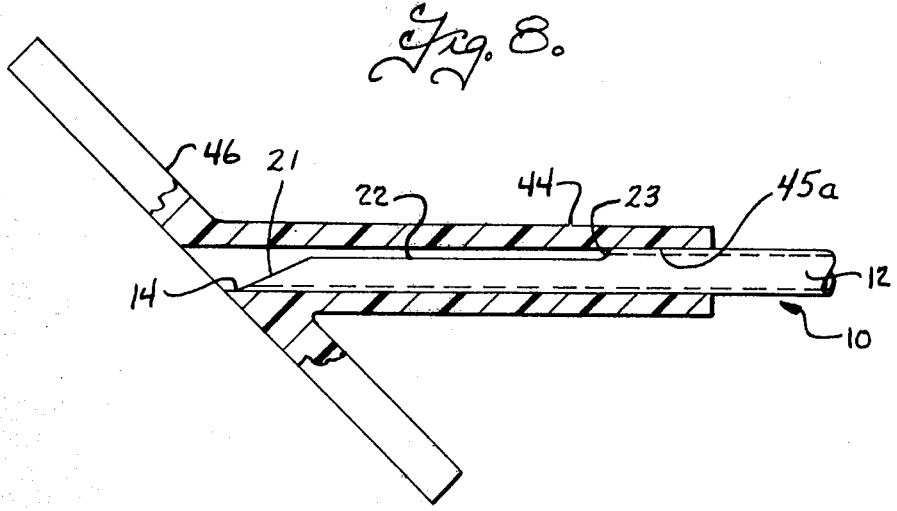

ASPIRATOR METHOD

CROSS REFERENCE

This application is a division of application Ser. No. 477,847, filed June 10, 1974, now U.S. Pat. No. 3,920,001, which was a continuation-in-part of application Ser. No. 58,049, filed July 24, 1970, now abandoned.

BACKGROUND

The invention pertains to instruments used in the field of medicine and more particularly to an aspirator and method for taking a blood sample.

In taking a blood sample, it is customary to insert the cannula into a vein and withdraw a sample into a syringe. In the use of a conventional cannula it is necessary to accurately position the point in the vein in such a manner that the opening at the point is not blocked. For example, an 18-gauge cannula has a lumen of about 0.03 inch diameter. If the penetrating point is at a 30° angle, the axial length of the end opening is only about 0.06 inch. This emphasizes the problem of accurately positioning the point. If the cannula is inserted too deeply, the point may pass through the vein and the opening will be blocked. If the opening is otherwise positioned adjacent the wall of the vein, it may be blocked, or it may become blocked when a slight vacuum is applied in drawing blood. It is desirable to have a device that alleviates the necessity of accurate positioning, without affecting the operability. Additionally, the material punctured by the cannula has a tendency to bulge into the lumen and cause what is commonly known as "coring" or "heel shaving". When this occurs, a piece of the material plugs the lumen so that it is difficult to draw a blood sample. It is desirable to have a device which alleviates the problem of "coring", without affecting the operability of the aspirator.

In the practice of pediatrics, it is frequently necessary to take a blood sample of an infant — perhaps a newborn baby. Such a sample may be taken from the femoral vein and, while it is usually possible to pierce the vein, to accurately position the point of a 25-guage cannula is difficult at best. The femoral vein is near the femur and this fact is used in taking the sample. A cannula is inserted in the infant's thigh until it contacts the femur, the cannula is then slowly retracted until the open end communicates with the femoral vein. Obviously this is a difficult operation. It is desirable to provide a method which alleviates the necessity of accurately positioning the end of the cannula.

SUMMARY

The present invention relates to an improved aspirator method.

It is an object of the present invention to provide a new and improved method for taking a blood sample and which is fully operative even when not exactly positioned.

These, and other objects and advantages of the present invention, will become apparent as the same becomes better understood from the following detailed description when taken in conjunction with the accompanying drawings.

DRAWINGS

FIG. 1 is a side elevational view of a preferred embodiment of the present invention mounted on a syringe;

FIG. 2 is a front view as seen from line 2—2 of FIG. 1;

FIG. 3 is a view of the back side of the disk as seen from line 3—3 of FIG. 1;

FIG. 4 is an enlarged fragmentary side elevational view of the apparatus shown inserted in a vein which is partially shown in vertical section to illustrate details;

FIG. 5 is an enlarged longitudinal sectional view through the sleeve and disk;

FIG. 6 is a cross-sectional view taken along line 6—6 of FIG. 5 and on a still larger scale;

FIG. 7 is a view similar to FIG. 4 but with the end of the cannula at a different position relative to the vein, and showing the lateral opening sealed by the sleeve; and FIG. 8 is a view similar to FIG. 5 but showing the lateral opening sealed by the sleeve.

DESCRIPTION

Reference is now made more particularly to the drawings which illustrate the best presently known mode of carrying out the invention and wherein similar reference characters indicate the same parts throughout the several views.

A cannula, generally designated 10, preferably has a size in the range of 25 guage to 16 guage and includes a tubular body 12 providing a lumen 13. At the distal end of the body 12 is a penetrating point 14 provided by about a 30° angle of the distal end. Thus the lumen terminates at what can be described as an opening 21 at the distal end of the cannula. A hub 16 is provided at the proximal end of the cannula for attachment to a syringe 18. The syringe provides a reservoir for receiving blood from the patient, and has a plunger 19 for applying a partial vacuum on the reservoir as the plunger is retracted. Such syringes are well known in the art and additional description is deemed unnecessary. It is contemplated, however, that the present invention can be used with other suitable apparatus for applying a slight vacuum to draw blood from a patient.

In use, the cannula 10 is inserted through the skin 32 and moved therebeneath through the subcutaneous tissue 34. The piercing point 14 pierces the wall of a vein 36 or other blood vessel and moves into the vessel. A conventional cannula is provided with an opening adjacent the penetrating point 14. In use it is possible to partially or completely block this opening. For example, should the opening be positioned adjacent the wall of the vein 36, the flow of blood will be restricted. Additionally, if the cannula is inserted too deeply, the penetrating point 14 may pass through the vein thereby necessitating repositioning.

In accordance with the present invention, the cannula is formed with a lateral opening 22 through the cannula wall. The lateral opening 22 (see FIG. 4) intersects the opening 21 at the end of the cannula and having a width less than 180° (see FIG. 6). The lateral opening provides an entrance for blood in the event that the open end is obstructed in any of the manners described above. The lateral opening 22 extends along the cannula to a remote end 23, a distance from the proximal end preferably in the range of 10 to 40 times the diameter of the lumen 13. For example, an 18 guage cannula has a lumen with a diameter of about 0.03 inch. For this size, the remote end 23 would be located between 0.3 inch and 1.2 inch from the proximal end of the cannula. In accordance with the present invention, it is essential that the cannula 10 have a smooth exterior surface with no obstructions thereon. For this purpose, the body 12 has a uniform outer diameter along its entire length.

It is essential to avoid introducing air into the vein 36 and also to avoid drawing air into the syringe 18 when taking a blood sample. For this purpose, a tubular sleeve 44 is provided to slidably surround the tubular body 12 of the cannula 10 and seal the lateral opening 22. It is necessary that the sleeve 44 seal to the tubular body 12 of the cannula prior to insertion (as shown in the position of FIG. 1 or FIG. 8), and that the cannula 10 be slidable extensible therethrough to the position shown in FIGS. 4, 5 or 7 where the lateral opening can communicate with the vein 36. For this purpose, sleeve 44 has a bore 45 for receiving the tubular body of the cannula. The sleeve 44 has a length greater than the distance from the penetrating point 14 to the remote end 23 of the lateral opening 22, as shown in FIG. 8. The bore 45 is sized to closely receive the tubular body 12 and provide an air-tight seal thereagainst; for example, note the seal area designated 45a in FIG. 8. Yet the bore 44 is sized to permit sliding movement between the cannula and sleeve, from the position shown in FIG. 1 all the way to the hub 16.

It is preferable to introduce the cannula 10 into the skin 32 and vein 36 at an angle to facilitate penetration by the piercing point 14. For this purpose, a disk or base 46 is mounted on the sleeve 44 at an oblique angle to the axis of the sleeve. The base 46 is adapted to be positioned on the surface of the skin 32 in overlying relation to the vein 36, and the cannula is then pushed through the sleeve 44 to penetrate the skin and enter the vein of the patient. In order to facilitate aligning the cannula with the vein, the base 46 is preferably formed of a clear material such as transparent plastic. By pressure applied against the base 46, it will seal against the skin 32 of the patient. A base of about ⅝ inch diameter is a suitable size for this purpose. An adhesive (not shown) can be applied to the underside of the base 46 to aid in holding the base and sleeve 46 in position over the vein and sealed against the skin 32.

In one preferred arrangement, the remote end 23 of the lateral opening 22 is ½ inch from the penetrating point 14, the sleeve 44 has a length of about ¾ inch, and the cannula is 18 guage, having a length of about 2 inches.

The importance of the sealing of the base 46 against the skin 32 and of the sleeve 44 over the lateral opening 22, is demonstrated in FIG. 7. If the vein 36 is close to the surface of the skin 32, it is sometimes possible to pierce the vein while some of the lateral opening 22 is still exterior of the skin. When this occurs, the lateral opening 22 is sealed by the sleeve 44 while the base 46 seals against the skin 32. Not only is a larger opening provided for receiving the blood, but a smaller area of the cannula penetrates the patient since the end 23 is still exterior. In such use, the lateral opening 22 is sealed by the sleeve 44, and the base 46 seals against the skin 32 throughout the procedure. The cannula 10 is aligned with the vein 36 and inserted into the vein until the lateral opening communicates with the vein, but without regard to whether the lateral opening 22 is still external of the skin. Thereafter, a slight vacuum is applied to withdraw the blood sample.

In taking a blood sample from an infant, the apparatus of the present invention is also advantageous. The cannula 10 is inserted into the infant's leg, through the femoral vein, until the penetrating point is adjacent the femur. In many instances, the lateral opening 22 will then be communicating with the femoral vein; however, the walls of the vein may be pinched together. Therefore, the cannula should be retracted slightly until proper communication is provided between the lateral opening and the femoral vein. Thereafter, a slight vacuum is applied to withdraw the blood sample.

It is now deemed apparent that the present invention provides an aspirator method which alleviates the necessity of accurately positioning the end of a cannula.

I claim:

1. A method of taking a blood sample from an infant utilizing a cannula having a penetrating point at its distal end and an elongate lateral opening through the cannula wall on the side opposite the penetrating point and intersecting the end opening, comprising the steps of:

providing a sleeve having a length greater than the length of the lateral opening and an outwardly-extending flat base at the end adjacent the penetrating point;

slidably mounting the sleeve on the cannula for movement between a first position where the penetrating point is inside the sleeve and the lateral opening is covered by the sleeve, and a position closer to the hub;

sealing the sleeve against the cannula to provide an air-tight cover extending over the lateral opening;

sealing the base against an infant's skin at a location above the femoral vein and maintaining the sealing against the skin throughout the sebsequent steps;

inserting the cannula into the infant's leg and through the femoral vein until the penetrating point is adjacent the femur, thereby sliding the cannula relative to the sleeve;

withdrawing the cannula until the lateral opening communicates with the femoral vein;

applying a slight vacuum on the cannula to withdraw blood therethrough; and thereafter withdrawing the cannula from the infant.

2. A method of taking a blood sample utilizing a cannula having a penetrating point at its distal end, comprising the steps of:

providing an elongate lateral opening through the cannula wall on the side opposite the penetrating point and intersecting the end opening, and extending along the cannula from the distal end a distance in the range of ten to forty times the diameter of the lumen of the cannula;

providing a sleeve having a length greater than the distance from the distal end to the remote end of the lateral opening and an outwardly-extending flat base at the end adjacent the penetrating point;

slidably mounting the sleeve on the cannula for movement between a first position where the penetrating point is inside the sleeve and the lateral opening is covered by the sleeve, and a position closer to the hub of the cannula;

sealing the sleeve against the cannula at the first position to provide an air-tight cover extending over the lateral opening;

sealing the base against a patient's skin at a location above a blood vessel of undetermined depth below the skin and maintaining the sealing against the skin throughout the subsequent steps;
aligning the cannula with the blood vessel and inserting the cannula into the patient to a depth sufficient to pierce the blood vessel and with the lateral opening communicating with the blood vessel and without regard to whether any portion of the lateral opening is still external of the skin; and
applying a slight vacuum on the cannula to withdraw blood therethrough.

* * * * *